US006486573B2

United States Patent
Yagi et al.

(10) Patent No.: US 6,486,573 B2
(45) Date of Patent: Nov. 26, 2002

(54) PORTABLE X-RAY FLUORESCENCE ANALYZER

(75) Inventors: Shigeki Yagi, Chiba (JP); Koichi Tamura, Chiba (JP)

(73) Assignee: Seiko Instruments Inc. (JP)

( * ) Notice: Subject to any disclaimer, the term of this patent is extended or adjusted under 35 U.S.C. 154(b) by 41 days.

(21) Appl. No.: 09/827,125

(22) Filed: Apr. 5, 2001

(65) Prior Publication Data

US 2001/0038248 A1 Nov. 8, 2001

(51) Int. Cl.⁷ .................................... H05G 1/54
(52) U.S. Cl. ........................ 307/328; 378/117
(58) Field of Search ................... 307/326–328; 378/102, 117, 44–50; 361/191–193

(56) References Cited

U.S. PATENT DOCUMENTS

| | | | | |
|---|---|---|---|---|
| 3,686,510 A | * | 8/1972 | Korb ......................... 361/192 |
| 4,775,993 A | * | 10/1988 | Kaul et al. ................. 378/117 |
| 5,212,621 A | * | 5/1993 | Panter ........................ 307/328 |
| 6,178,227 B1 | * | 1/2001 | Sato ........................... 378/117 |
| 2001/0038248 A1 | * | 11/2001 | Yagi et al. .................. 307/328 |
| 2001/0038520 A1 | * | 11/2001 | Yagi ........................... 361/246 |

\* cited by examiner

*Primary Examiner*—Fritz Fleming
(74) *Attorney, Agent, or Firm*—Adams & Wilks

(57) ABSTRACT

A portable X-ray fluorescence analyzer has a measurement head section and an operating section. An X-ray source is disposed in the measurement head section for irradiating X-rays onto a sample for analysis of the sample utilizing principles of X-ray fluorescence. A power source is disposed in the operating section for supplying a voltage to the X-ray source to irradiate X-rays. A control circuit controls the power source to supply a voltage to the X-ray source through a first X-ray switch disposed in the measurement head section and a second X-ray switch disposed in the operating section by ON/OFF control of the first and second X-ray switches. A safety switch is disposed in the measurement head section for interlocking the first and second X-ray switches so that the control circuit controls the power source to supply a voltage to the X-ray source to irradiate X-rays only when the safety switch and the first and second X-ray switches are switched to an ON state.

9 Claims, 2 Drawing Sheets

PORTABLE X-RAY FLUORESCENCE ANALYZER

FIELD OF THE INVENTION

The present invention relates to a portable fluorescent X-ray analyzer mainly aimed at outdoor elementary analysis, such as archaeological sample examination, criminal field searches, fire patrol searches, scrap article inspection etc.

BACKGROUND INFORMATION

In the case of a portable X-ray fluorescence analyzer comprising a measurement head and an operating section, in order to make ordinary operations efficient there are two operators, one for arranging the measurement head facing towards a sample, and another operating the operating section to collect measurement data, and the two operators co-operate with each other to perform measurement.

A portable X-ray fluorescence analyzer of the related art has a switch for designating X-ray generation provided in one of either the measurement head or the operating section, and the generation or suspension of X-rays is entrusted to a single operator.

For this reason, there is a drawback, from the point of view of the operator who does not operate the switch constituting the X-ray generation/suspension means, that X-ray generation or suspension can also be carried out in an unfavorable situation.

SUMMARY OF THE INVENTION

The present invention has as its object to provide an extremely safe portable X-ray fluorescence analyzer to overcome the above described problems in the conventional art.

In order to achieve the above described object, the present invention is a portable X-ray fluorescence analyzer, in which an X-ray switch is attached to both a measurement head and an operating section, and in a state where a safety switch arranged on the measurement head is ON, X-rays are only generated when both of the X-ray switches are operated at the same time.

Furthermore, if the safety switch provided on the measurement head is turned OFF to stop X-rays, even if the safety switch is turned on again, it is not possible to generate X-rays until both the measurement head side X-ray switch and the operating section side X-ray switch are momentarily turned OFF.

Further, display means for indicating that X-rays can not be generated when the safety switch is turned OFF and the measurement head side X-ray switch and the operating section side X-ray switch both remain ON, unless both the measurement head side X-ray switch and the operating section side X-ray switch are turned OFF, is provided in at least the measurement head or the operating section.

DETAILED DESCRIPTION OF THE PREFERRED EMBODIMENT

In a portable X-ray fluorescence analyzer, if a measuring head side X-ray switch and an operating section X-ray switch are turned on while a safety switch provided in the measuring head is turned on, X-rays will be generated.

Also, if the safety switch provided on the measurement head is turned off to stop X-rays, after the safety switch has been turned on again, if both the measurement head side X-ray switch and the operating section side X-ray switch are turned on again after both being momentarily turned off, X-rays are generated.

The present invention improves operational efficiency of a portable X-ray fluorescence analyzer comprising a measurement head and an operation section, by providing a structure in which X-ray switches are attached to both the measurement head and the operating section and X-rays are only generated when both the X-ray switches are turned on at the same time while a safety switch provided in the measurement head is on, thus making it possible to cause generation of X-rays in a state capable of ensuring adequate safety to an operator on the measurement head side, and making it possible for either operator to stop X-rays at any time on their own.

Further, in the case where a safety interlock is operated to stop X-rays, and X-rays are to be generated again after the interlock has been released, it is necessary to momentarily turn both the measurement head side X-ray switch and the operation section X-ray switch off. In this way, it is possible to provide an extremely safe, portable X-ray fluorescence analyzer.

EMBODIMENT

An embodiment of the present invention will be described in the following based on the drawings.

Figure 1:
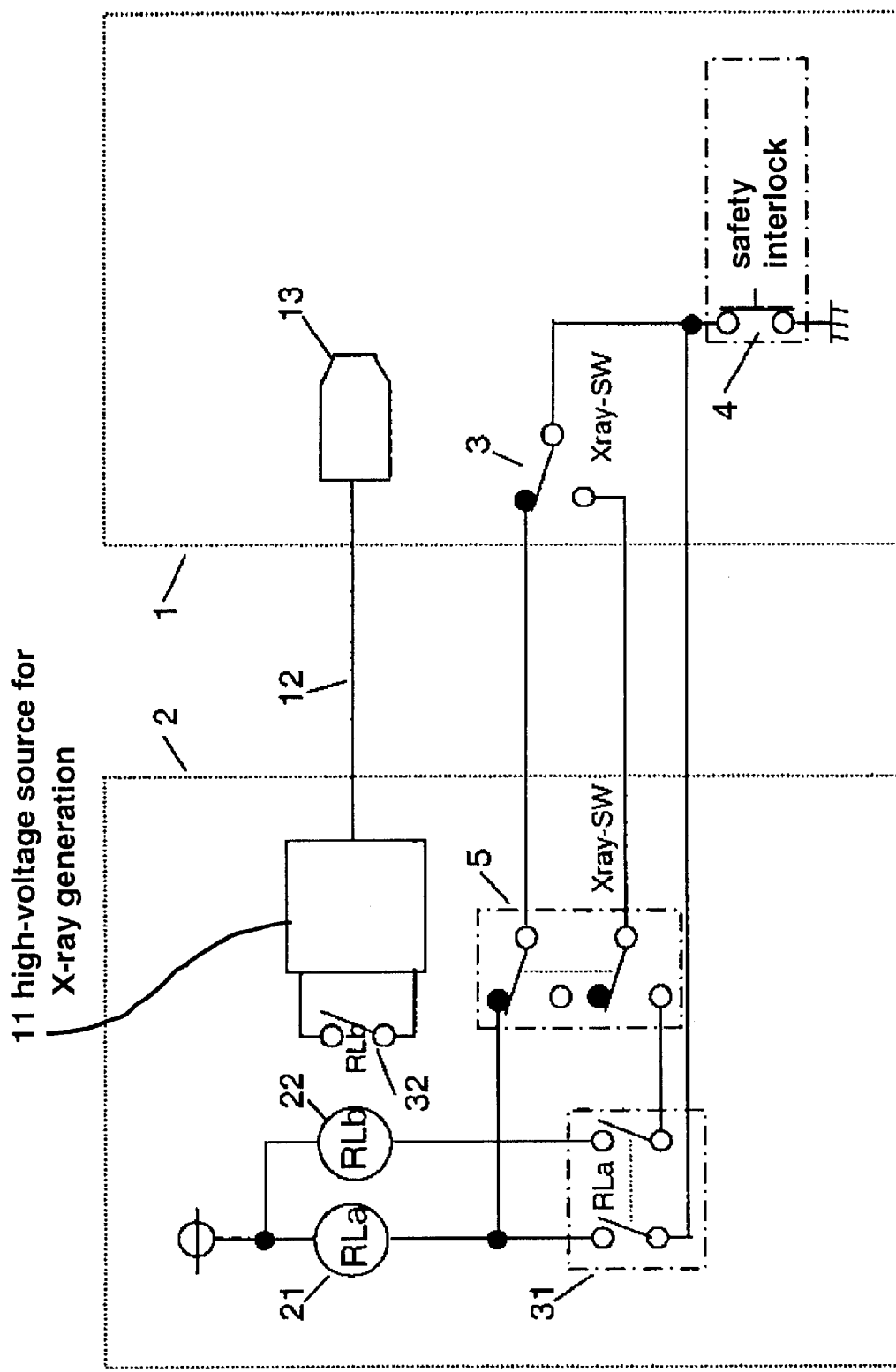
FIG. 1 is a circuit diagram of an embodiment of a portable X-ray fluorescence analyzer of the present invention.
Figure 2:
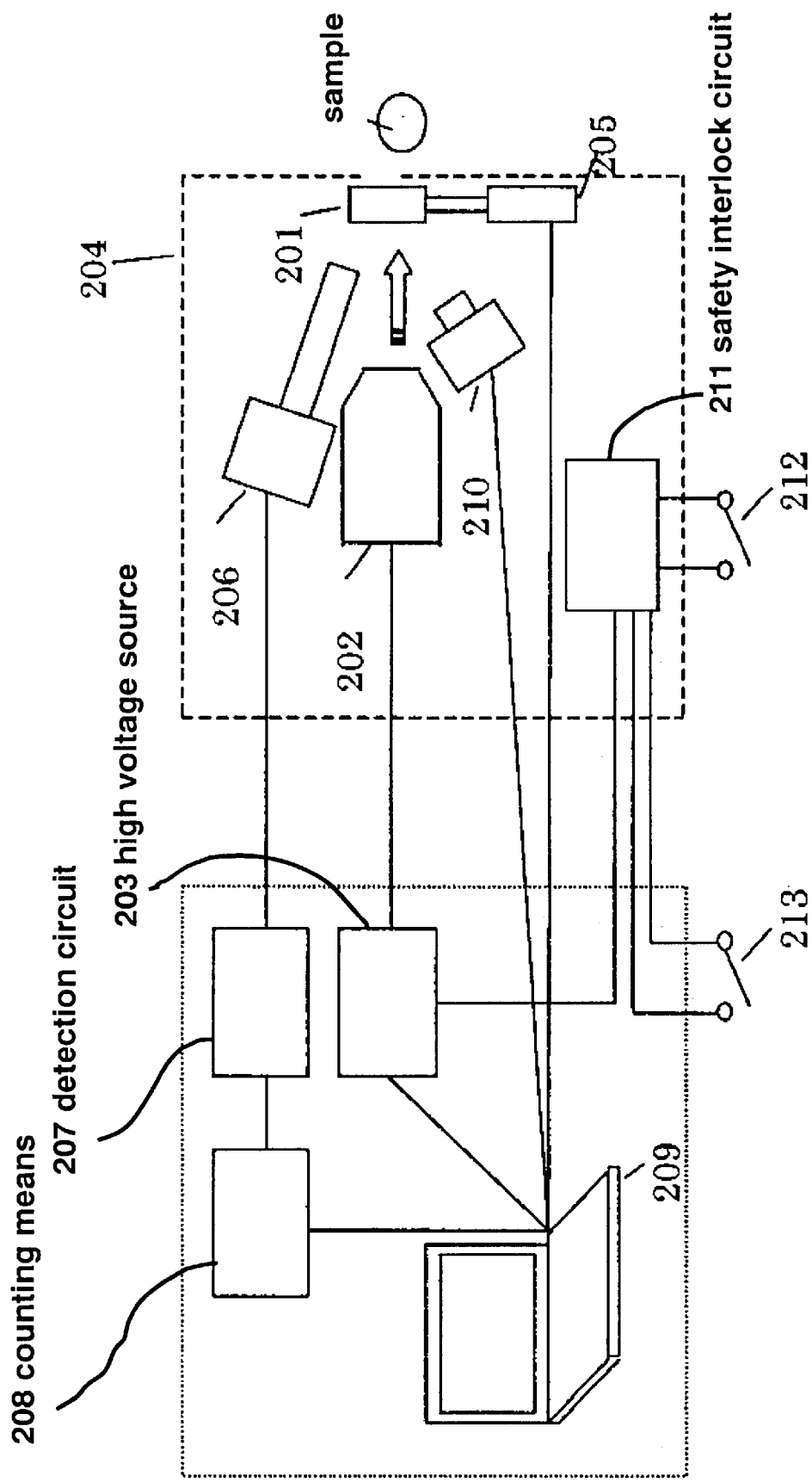
FIG. 2 is an overall schematic diagram of an embodiment of a portable X-ray fluorescence analyzer of the present invention.

FIG. 1 is a circuit diagram of an embodiment of a portable X-ray fluorescence analyzer of the present invention. In the circuit diagram of FIG. 1, parts that are related to X-ray generation within the structure of the portable X-ray fluorescence analyzer are shown extracted. FIG. 2 is an overall schematic diagram of an embodiment of a portable X-ray fluorescence analyzer of the present invention. A shutter 201 in FIG. 2 is made of metal of a sufficient thickness to be able to completely shield against X-rays. An X-ray vessel 202 is realized as a small lightweight device by adopting an end window type small X-ray vessel. Luminous flux of X-ray fluorescence generated from the X-ray vessel 202 that receives a high voltage supply from a high voltage source 203 passes through a roentgenization space provided in a measurement head housing 204 of the X-ray fluorescence analyzer, and are irradiated onto a sample to measured, but while measurement is not in progress the X-rays are shielded by the shutter 201 and there is no leakage of X-rays to parts outside the measurement head. The shutter is mechanically operated by an actuator such as a solenoid. Luminous flux of secondary emissions of X-ray fluorescence from the sample to be measured by X-ray irradiation are taken in by an X-ray detector 206, converted to an electrical pulse signal and transmitted to a subsequent detection circuit. As the X-ray detector 206, it is possible to use a semiconductor detector of Si or Ge, a scintillation detector, or a proportional counter tube etc., depending on the purpose of measurement. In the detection circuit 207, an inputted electrical pulse signal is amplified so as to make it a signal level that is easy to process later. Appropriate waveform adjustment processing so as to ensure a required counting rate and obtain a favorable energy resolution is also performed at this time. The wave height of the electrical pulse after this processing has been performed is converted to a digital value by an A/D converter, and then passed to subsequent counting means 208. In the counting means 208, the number of electrical pulses inputted during the measurement period is counted peak-to-peak. Successively detected secondary X-ray fluorescence is then expressed as a spectrum having a shape representing totals of X-rays, i.e. energy.

Movement instructions for the shutter 201, output condition settings for the high voltage source 203, and display and analysis of count results are implemented by a computer 209.

In order to irradiate primary X-rays on sections to be measured, it is necessary to accurately position the measurement head housing 204. An imaging device, such as a CCD camera, is provided on the measurement head housing 204 side, and by optically observing the sample to be measured, a positional relationship between the sample to be measured and the measurement head housing 204 can be simply ascertained, and accurate measuring position alignment becomes possible.

When detecting anomalies in mounting states of the portable X-ray fluorescence analyzer and operational anomalies of components relating to device safety, the output of the high voltage source 203 is controlled, and a safety interlock circuit 211 is provided in the ordinary portable X-ray fluorescence analyzer, with the intention of stopping generation of X-rays. The generation and stopping of X-rays is instructed using X-ray key switches 212 and 213, but with respect to stopping X-rays, operation of the safety interlock circuit 211 has priority.

The portable X-ray fluorescence analyzer has structural elements divided into the measurement head section and the operating section in order to improve portability, and the measurement head sections are preferably made small and light in weight.

In FIG. 1, the high voltage source 11 for X-ray generation is provided on the operation section 2 side. Output of this X-ray generation high voltage source 11 is connected to the X-ray tube 13 provided on the measurement head 1 side, through a high voltage cable 12. If a contact point 32 of relay b22 is closed, the X-ray generation high voltage source 11 generates a high voltage and X-rays are generated from the X-ray tube 13. The safety switch 4 is normally in the ON state, but is linked to the device safety interlock circuit and becomes off at the time of a device installation abnormality or an operational abnormality of components relating to device safety. First of all, with this safety switch 4 on, when the measurement head 1 side X-ray switch 3 and the operation section 2 side X-ray switch 5 are off at the same time current flows in a coil of the relay a21, and the contact point 31 of the relay a21 is closed. By closing the contact point 31 of the relay a21, a current path is established from the power source through the coil of the relay a21, the contact point 31 of the relay a21, the safety switch 4 and ground, and the relay a21 is held in the on state as long as the safety switch 4 is not turned off. Next, if the measurement head 1 side X-ray switch 3 and the operation section 2 side X-ray switch 5 are turned on at the same time current flows in a coil of the relay b22, and the contact point 32 of the relay b22 is closed. As described above, if the contact point 32 of relay b22 is closed, the X-ray generation high voltage source 11 generates a high voltage and X-rays are generated from the X-ray tube 13.

If the safety switch 4 should be turned off for any reason, the current supply path for the coil of the relay b21 is broken, and the contact point 32 of the relay b22 opens. As a result, generation of X-rays is stopped. At this time the current supply path for the coil of the relay a21 is also broken, and so contact point 31 of the relay a21 opens. If this happens, even if the safety switch 4 is returned to the ON state, the current supply path for the coil of the relay b22 is not completed, and so with no further action X-rays are not generated again. After that, if the measurement head 1 side X-ray switch 3 and the operation section 2 side X-ray switch 5 are momentarily turned off at the same time, current flows in a coil of the relay a21, and the contact point 31 is closed. Then, if the measurement head 1 side X-ray switch 3 and the operation section 2 side X-ray switch 5 are turned on again at the same time current flows in the coil of the relay b22, the contact point 32 is closed, and as a result X-rays are generated again.

Here, by providing display means (for example, illumination using an led, or display on a screen of the computer 209) for indicating that x-rays can not be generated when the safety switch is turned off and the measurement head side x-ray switch and the operating section side x-ray switch both remain on, unless both the measurement head side x-ray switch and the operating section side x-ray switch are turned off, in at least one of the measurement head or the operating section, it becomes possible to recognize the current state of the switches.

What is claimed is:

1. A portable X-ray fluorescence analyzer comprising: a measurement head section; an X-ray source disposed in the measurement head section for irradiating X-rays onto a sample for analysis of the sample utilizing principles of X-ray fluorescence; an operating section; a power source disposed in the operating section for supplying a voltage to the X-ray source to irradiate X-rays; a control circuit for controlling the power source to supply a voltage to the X-ray source through a first X-ray switch disposed in the measurement head section and a second X-ray switch disposed in the operating section by ON/OFF control of the first and second X-ray switches; and a safety switch disposed in the measurement head section for interlocking the first and second X-ray switches so that the control circuit controls the power source to supply a voltage to the X-ray source to irradiate X-rays only when the safety switch and the first and second X-ray switches are switched to an ON state.

2. A portable X-ray fluorescence analyzer according to claim 1; wherein when the safety switch is switched to an OFF state the X-ray source stops irradiating X-rays, and subsequent switching of the safety switch to the ON state does not permit the X-ray source to irradiate X-rays until both of the first and second X-ray switches are momentarily switched to an OFF state and then switched to the ON state.

3. A portable X-ray fluorescence analyzer according to claim 2; further comprising display means disposed in at least one of the measurement head section and the operating section for displaying that the X-ray source cannot irradiate X-rays when the safety switch is in the OFF state and the first and second X-ray switches remain in the ON state until both of the first and second X-ray switches are momentarily switched to the OFF state and then the safety switch and the first and second X-ray switches are switched to the ON state.

4. A portable X-ray fluorescence analyzer according to claim 1; wherein each of the measurement head section and the operating section has a portable configuration.

5. A portable X-ray fluorescence analyzer comprising: a housing having a measurement head section and an operating section; an X-ray source disposed in the measurement head section of the housing for irradiating X-rays onto a sample for analysis of the sample utilizing principles of X-ray fluorescence; a power source disposed in the operating section of the housing for supplying a voltage to the X-ray source to irradiate X-rays; a pair of X-ray switches each disposed in a respective one of the measurement head section and the operating section of the housing for permitting the X-ray source to irradiate X-rays in an ON state of the X-ray switches and for stopping the X-ray from irradiating X-rays in an OFF state of the X-ray switches; and a safety interlock circuit having a safety switch for overriding the X-ray switches in the ON state thereof to stop the X-ray source from irradiating X-rays in an OFF state of the safety switch and for permitting the X-ray source to irradiate X-rays in an ON state of the safety switch; whereby the X-ray source irradiates X-rays only when the X-ray switches and the safety switch are simultaneously in the ON state.

6. A portable X-ray fluorescence analyzer according to claim 5; wherein when the safety switch is in the OFF state and the X-ray switches are in the ON state, switching of the safety switch to the ON state does not permit the X-ray source to irradiate X-rays until the X-ray switches are momentarily switched to the OFF state and then switched to the ON state.

7. A portable X-ray fluorescence analyzer according to claim 5; wherein the housing has a portable configuration.

8. A portable X-ray fluorescence analyzer according to claim 5; wherein the measurement head section of the housing has an opening through which the X-ray source irradiates X-rays onto the sample located outside of the housing.

9. A portable X-ray fluorescence analyzer according to claim 8; further comprising an X-ray detector disposed in the measurement head section of the housing for detecting fluorescent X-rays reflected by the sample through the opening.

* * * * *